United States Patent [19]

Taniguchi

[11] Patent Number: 5,180,849

[45] Date of Patent: Jan. 19, 1993

US005180849A

[54] PROCESS FOR PRODUCING PURIFIED TEREPHTHALIC ACID

[75] Inventor: Norio Taniguchi, Wakicho, Japan

[73] Assignee: Mitsui Petrochemnical Industries, Ltd., Tokyo, Japan

[21] Appl. No.: 725,426

[22] Filed: Jul. 3, 1991

[30] Foreign Application Priority Data

Jul. 4, 1990 [JP] Japan .................................. 2-177965

[51] Int. Cl.$^5$ .................... C07C 51/265; C07C 51/487
[52] U.S. Cl. ..................................... 562/414; 562/487
[58] Field of Search ................................. 562/487, 414

[56] References Cited

U.S. PATENT DOCUMENTS

| | | | |
|---|---|---|---|
| 4,629,715 | 12/1986 | Schroeder | 502/185 |
| 4,791,226 | 12/1988 | Puskas et al. | 562/487 |
| 4,808,751 | 2/1989 | Schroeder et al. | 562/487 |
| 4,833,269 | 5/1989 | Schroeder | 562/487 |
| 4,892,972 | 1/1990 | Schroeder et al. | 562/487 |

Primary Examiner—Jose G. Dees
Assistant Examiner—Vera C. Clarke
Attorney, Agent, or Firm—Sherman & Shalloway

[57] ABSTRACT

In a process for producing purified terephthalic acid which comprises catalytically oxidizing p-xylene in liquid phase to produce crude terephthalic acid containing 4-carboxybenzaldehyde as a main impurity therein, and treating the crude terephthalic acid with hydrogen in the presence of hydrogenation catalyst in a reaction vessel, thereby to produce purified terephthalic acid containing 4-carboxybenzaldehyde in an amount of fixed range in a stationary manner, there is provided an improvement which makes it possible for the treatment to reach the stationary state promptly after partial exchange of deactivated catalyst for a new one. The improvement comprises feeding into the reactor crude terephthalic acid which contains 4-carboxybenzaldehyde in an amount larger than that in the stationary state of the treatment, and treating the terephthalic acid until the treatment reaches the stationay state.

6 Claims, No Drawings

PROCESS FOR PRODUCING PURIFIED TEREPHTHALIC ACID

FIELD OF THE INVENTION

This invention relates to a process for producing purified terephthalic acid. More particularly, it relates to an improvement in the process for producing purified terephthalic acid containing 4-carboxybenzaldehyde as a main impurity in an amount of fixed small range in a stationary manner.

DESCRIPTION OF THE PRIOR ART

Purified terephthalic acid is needed for the production of polyester fibers. Such purified terephthalic acid has been heretofor produced by, for example, such a process as described in Japanese Patent Publication No. 41-16860. According to the process, p-xylene is catalytically oxidized in liquid phase to produce crude terephthalic acid usually containing 4-carboxybenzaldehyde as a main impurity in an amount of 0.1-0.4% by weight, the crude terephthalic acid is fed as an aqueous slurry into a reaction vessel and made into an aqueous solution under a high temperature and pressure, and is treated with a hydrogenation catalyst exemplified by a granulated palladium catalyst supported on activated carbon. When the treatment of the crude terephthalic acid is carried out in a stationary manner, the resultant purified terephthalic acid usually contains 1-25 ppm of 4-carboxybenzaldehyde.

However, the efficiency of treating the crude terephthalic acid to hydrogenate the 4-carboxybenzaldehyde to p-methylbenzoic acid is reduced with time in the above process for the production of purified terephthalic acid by various reasons, mainly by reason of deactivation of hydrogenation catalyst. Accordingly, the catalyst is usually exchanged at regular intervals in the process.

In general, a hydrogenation catalyst has a high initial activity. Thus, in working the above process for the purified terephthalic acid, when a catalyst is deactivated and such a deactivated catalyst is entirely exchanged for a new one, undesirable by-products are produced by excessive hydrogenation reaction, but also an excessive amount of 4-carboxybenzaldehyde is reduced, thereby to cause a decrease in stability of purity of the produced terephthalic acid. Moreover, at the restart of the treatment, the crude terephthalic acid is adsorbed on the activated carbon of the catalyst to generate heat, so that the catalyst is liable to break to pieces. The broken catalyst may mix with the resultant terephthalic acid.

Therefore, for the purpose of lengthening the life of hydrogenation catalyst used in the process, there is disclosed in East German Patent No. 212,162 that the deactivated catalyst in a reaction vessel is not entirely exchanged for a new one, but only a part of the catalyst is exchanged for a new one while the deactivated catalyst is again used as it is together with the exchanged new one.

According to this method, the life of catalyst may be lengthened, but there is needed much time for the stationary state to be reached in which the treatment of the crude terephthalic acid provides in a stationary manner purified terephthalic acid containing 4-carboxybenzaldehyde in an amount of fixed small range after the partial exchange of catalyst. Such a prolonged time to reach the stationary state brings about a great deal of loss in raw materials as well as undesirable production of terephthalic acid outside the standard.

BRIEF SUMMARY OF THE INVENTION

Therefore, it is an object of the invention to provide an improvement in a process for the production of purified terephthalic acid which comprises treating crude terephthalic acid with hydrogen in the presence of hydrogenation catalyst, the improvement making it possible for the treatment to reach the stationary state promptly after partial exchange of the catalyst.

In accordance with the invention, there is provided an improvement in a process for producing purified terephthalic acid which comprises catalytically oxidizing p-xylene in liquid phase to produce crude terephthalic acid containing 4-carboxybenzaldehyde as a main impurity therein, and treating the crude terephthalic acid with hydrogen in the presence of a hydrogenation catalyst in a reaction vessel, thereby to produce purified terephthalic acid containing 4-carboxybenzaldehyde in an amount of fixed range in a stationary manner at a temperature of 255°-300° C. and under a pressure of 10-110 $Kg/cm^2$ with a partial pressure of hydrogen being 0.5-20 $Kg/cm^2$, the improvement comprising exchanging the catalyst in the reaction vessel in part for a new one when the catalyst is deactivated, and thereafter feeding into the reactor crude terephthalic acid which contains 4-carboxybenzaldehyde in an amount larger than that in the stationary state of the treatment for restarting the treatment of the crude terephthalic acid, and treating the terephthalic acid until the treatment reaches the stationary state.

There is also provided a further improvement of the invention in the process, which comprises exchanging the catalyst in the reaction vessel in part for a new one when the catalyst is deactivated, and thereafter treating the crude terephthalic acid under a partial pressure of hydrogen smaller than that in the stationary state.

DETAILED DESCRIPTION OF THE INVENTION

Herein the specification, by the stationary state of treatment is meant the state of treatment which provides in a stable and stationary manner purified terephthalic acid containing 4-carboxybenzaldehyde in an amount of fixed small range in the treatment of crude terephthalic acid containing 4-carboxybenzaldehyde as a main impurity with hydrogen in the presence of hydrogenation catalyst to produce the purified terephthalic acid. The crude terephthalic acid is obtained by the catalytic oxidation of p-xylene in liquid phase.

The deactivation of hydrogenation catalyst may be detected by an increase of content of 4-carboxybenzaldehyde in the resultant purified terephthalic acid. Furthermore, the quality of terephthalic acid produced is usually related with transmittance at 340 nm. Thus, in the industrial production of purified terephthalic acid, the purity of terephthalic acid as the product is determined by content of 4-carboxybenzaldehyde and transmittance at 340 nm. These control values are maintained within a fixed range when the treatment is carried out in a stationary manner. When the control values have come outside the fixed range, it is necessary that the catalyst in the reaction vessel be partly exchanged for a new one to increase the efficiency of the treatment.

After the partial exchange of catalyst and when the hydrogenation of crude terephthalic acid has been restarted, the resultant purified terephthalic acid usually has a very small content of 4-carboxybenzaldehyde on account of high activity of catalyst, and accordingly the resultant purified terephthalic acid has a high transmittance at 340 nm.

Although depending upon the degree of deactivation of catalyst, usually 20-70% of the deactivated catalyst in a reaction vessel is exchanged for a new one. After the deactivated catalyst in the reaction vessel has been in part exchanged with a new one in a manner as above, an aqueous slurry of crude terephthalic acid is fed into the reaction vessel and made into an aqueous solution under a high temperature and pressure to restart the treatment.

According to the invention, crude terephthalic acid containing 4-carboxybenzaldehyde in a larger amount than that in the stationary state is fed into the reaction vessel after the reaction is stabilized until the stationary state is reached. Alternatively, the treatment is carried out under a partial pressure of hydrogen smaller than that in the stationary state. Of course, crude terephthalic acid containing 4-carboxybenzaldehyde in a larger amount than that in the stationary state may be fed into the reaction vessel and treated under a partial pressure of hydrogen smaller than that in the stationary state until the stationary state of the reaction is reached. This operation reduces the time in which the reaction reaches the stationary state.

In the stationary state of the treatment, the crude terephthalic acid is usually fed into the reaction vessel as an aqueous solution containing 24-30% by weight of terephthalic acid. The hydrogenation treatment is carried out usually at temperatures of 255°-300° C. under pressures of 10-110 Kg/cm$^2$ and a partial pressure of hydrogen of 0.5-20 Kg/cm$^2$.

The hydrogenation catalyst used includes, for example, palladium, ruthenium, rhodium, osmium, iridium, platinum, platinum black, palladium black, iron, or cobalt-nickel, each supported on activated carbon.

EXAMPLES

The invention will now be more specifically set forth with reference to examples, however, the invention is not limited thereto.

A reaction will be first set forth which uses a deactivated hydrogenation catalyst (used in examples hereinafter) to illustrate the activity of the catalyst.

Reference Example 1

An amount of 30 g of crude terephthalic acid containing 3600 ppm of 4-carboxybenzaldehyde and 210 g of water were placed in a 500 ml capacity autoclave together with 0.3 g of 0.5% by weight palladium supported on activated carbon, and the mixture was heated to 280° C. under stirring. Then, hydrogen was introduced into the autoclave so that the partial pressure of hydrogen was 7 Kg/cm$^2$G, followed by one hour treatment of the crude terephthalic acid.

The resultant purified terephthalic acid was found to contain 400 ppm of 4-carboxybenzaldehyde.

In the following examples, the deactivated catalyst was partly exchanged for a new one, and the treatment was carried out for one hour of crude terephthalic acid containing varied amounts of 4-carboxybenzaldehyde and/or under varied partial pressures of hydrogen to hydrogenate the 4-carboxybenzaldehyde.

Then, it was examined if the stationary state was reached in the above one hour treatment by determining the content of 4-carboxybenzaldehyde contained in the resultant purified terephthalic acid. Herein the examples, the stationary state was deemed to be reached when the content of 4-carboxybenzaldehyde in the resultant purified terephthalic acid was in the range of 10-12 ppm, as in the examples 4 and 8 as illustrated hereinafter.

EXAMPLE 1

A mixture of 0.03 g of the same deactivated catalyst as in the reference example 1 and 0.27 g of new one was used in the treatment as a hydrogenation catalyst.

An amount of 30 g of crude terephthalic acid containing 3600 ppm of 4-carboxybenzaldehyde and 210 g of water were placed in a 500 ml capacity autoclave together with 0.3 g of the above catalyst, and the mixture was heated to 280° C. under stirring. Then, hydrogen was introduced into the autoclave so that the partial pressure of hydrogen was 2 Kg/cm$^2$G, followed by one hour treatment.

The resultant purified terephthalic acid was found to contain 10 ppm of 4-carboxybenzaldehyde.

EXAMPLES 2-8

Using 0.3 g of mixture of the same deactivated catalyst as in the reference example 1 and a new one in a ratio as indicated in the table 1, the treatment of crude terephthalic acid was carried out in the same manner as in the example 1 with crude terephthalic acid containing varied amounts of 4-carboxybenzaldehyde and/or under varied partial pressures of hydrogen to hydrogenate the 4-carboxybenzaldehyde.

The content of 4-carboxybenzaldehyde contained in the resultant purified terephthalic acid is indicated in the table 1.

COMPARATIVE EXAMPLES 1-7

Using 0.3 g of mixture of the same deactivated catalyst as in the reference example 1 and a new one in a ratio as indicated in the table 1, the treatment was of crude terephthalic acid was carried out in the same manner as in the example 1 under varied partial pressures of hydrogen.

The content of 4-carboxybenzaldehyde contained in the resultant purified terephthalic acid is indicated in the table 1.

TABLE 1

|  | Reference Example 1 | Examples | | | | | | | |
|---|---|---|---|---|---|---|---|---|---|
|  |  | 1 | 2 | 3 | 4 | 5 | 6 | 7 | 8 |
| Catalyst Ratio[1] | 10/0 | 1/9 | 2/8 | 5/5 | 7/3 | 5/95 | 1/9 | 2/8 | 8/2 |
| Partial Pressure of Hydrogen (Kg/cm$^2$G) | 7 | 2 | 3 | 4 | 11 | 2 | 4 | 5 | 11 |
| Content of 4-CBA[2] (ppm) | | | | | | | | | |
| In Crude TA[3] | 3600 | 3600 | 3600 | 3600 | 3600 | 4200 | 4200 | 4200 | 2400 |
| In Purified TA[3] | 400 | 10 | 11 | 11 | 12 | 10 | 11 | 11 | 12 |

TABLE 1-continued

|  | Comparative Examples | | | | | | |
| --- | --- | --- | --- | --- | --- | --- | --- |
|  | 1 | 2 | 3 | 4 | 5 | 6 | 7 |
| Catalyst Ratio[1] | 1/9 | 2/8 | 5/5 | 7/3 | 8/2 | 5/95 | 8/2 |
| Partial Pressure of Hydrogen ($Kg/cm^2 G$) | 7 | 7 | 7 | 7 | 7 | 2 | 11 |
| Content of 4-CBA[2] (ppm) | | | | | | | |
| In Crude TA[3] | 3600 | 3600 | 3600 | 3600 | 3600 | 3600 | 3600 |
| In Purified TA[3] | below 1 | 1 | 2 | 60 | 140 | 2 | 38 |

Notes:
[1] Deactivated Catalyst/New Catalyst
[2] 4-Carboxybenzaldehyde
[3] Terephthalic acid The examples 1–3 carried out the treatment under a smaller partial pressure of hydrogen (2–4 $Kg/cm^2$ G) then the partial pressure of hydrogen (11 $Kg/cm^2$ G) in the stationary state (as in the example 4 wherein the crude terephthalic acid contained 3600 ppm of 4-carboxybenzaldehyde, and the resultant purified terephthalic acid contained 10–12 ppm of 4-carboxybenzaldehyde).

Thus, the examples 1–3 illustrate that terephthalic acid of the same quality as in the stationary state is obtained within one hour from the restart of the treatment. Accordingly, the partial pressure of hydrogen may then be raised to 11 $Kg/cm^2$ G to carry out the treatment in a stationary manner.

Meanwhile the examples 1–4 indicate the progress of deactivation of catalyst with time. These examples illustrate that the stationary state is reached within one hour when the treatment is restarted under a smaller partial pressure of hydrogen than that under the stationary state.

The examples 5–7 carried out the treatment under a smaller partial pressure of hydrogen (2–5 $Kg/cm^2$ G) than the partial pressure of hydrogen (11 $Kg/cm^2$ G) in the stationary state (as in the example 8 wherein the crude terephthalic acid contained 2400 ppm of 4-carboxybenzaldehyde and the resultant purified terephthalic acid contained 12 ppm of 4-carboxybenzaldehyde) by use of crude terephthalic acid containing 4200 ppm of 4-carboxybenzaldehyde.

Thus, the examples 5–7 illustrate that terephthalic acid of the same quality as in the stationary state is obtained within one hour from the restart of the treatment. Thereafter, the partial pressure of hydrogen may be raised to 11 $Kg/cm^2$ G while the content of 4-carboxybenzaldehyde in the crude terephthalic acid is reduced to 2400 ppm to carry out the treatment in a stationary manner as indicated in the example 8.

Meanwhile the examples 5–8 indicate the progress of deactivation of catalyst with time. These examples illustrate that the stationary state of treatment of crude terephthalic acid is reached within one hour when the treatment is restarted under a smaller partial pressure of hydrogen than that under the stationary state.

In contrast, the comparative examples 1–3 are corresponding to the examples 1–3, respectively, in respect of the deactivation of catalyst with time and the content of 4-carboxybenzaldehyde in the crude terephthalic acid. However, the treatment was carried out under a partial pressure of hydrogen not so small enough as compared with that of the stationary state, namely, under a partial pressure of hydrogen of 7 $Kg/cm^2$. Accordingly, in these comparative examples, the content of 4-carboxybenzaldehyde in the resultant terephthalic acid was very small after one hour treatment, and stationary state was not attained within one hour from the restart of the treatment.

The comparative examples 4 and 5 illustrate the treatment by use of further deactivated catalyst. In these examples, there is obtained no terephthalic acid of intended purity on account of excessive deactivation of catalyst.

The comparative examples 6 and 7 correspond to the examples 5 and 8, respectively. As seen in the example 5 in contrast to the comparative example 6, the stationary state is promptly reached by increasing the content of 4-carboxybenzaldehyde in the crude terephthalic acid used at the restart of the treatment. However, when the catalyst is more deactivated as seen in the comparative example 7 compared with the comparative example 6, the stationary state is not reached.

What is claimed is:

1. In a process for producing purified terephthalic acid which comprises catalytically oxidizing p-xylene in liquid phase to produce crude terephthalic acid containing 4-carboxybenzaldehyde as a main impurity therein, and treating the crude terephthalic acid with hydrogen in the presence of a palladium, ruthenium, rhodium, osmium, iridium, platinum, platinum black, palladium black, iron, or cobalt-nickel hydrogenation catalyst in a reaction vessel, thereby to produce purified terephthalic acid containing 4-carboxybenzaldehyde in an amount of fixed range in a stationary manner at a temperature of 255°–300° C. and under a pressure of 10–110 $Kg/cm^2$ with a partial pressure of hydrogen being 0.5–20 $Kg/cm^2$, the improvement comprising exchanging the hydrogenation catalyst in the reaction vessel in part for a new one when the catalyst is deactivated, and thereafter feeding into the reactor crude terephthalic acid which contains 4-carboxybenzaldehyde in an amount larger than that in the stationary state of the treatment for restarting the treatment of the crude terephthalic acid, and treating the terephthalic acid until the treatment reaches the stationary state.

2. The improvement as claimed in claim 1 wherein 20–70% of the deactivated catalyst is exchanged for a new one.

3. The improvement as claimed in claim 1 wherein the hydrogenation catalyst is granulated palladium supported on activated carbon.

4. In a process for producing purified terephthalic acid which comprises catalytically oxidizing p-xylene in liquid phase to produce crude terephthalic acid containing 4-carboxybenzaldehyde as a main impurity therein, and treating the crude terephthalic acid with hydrogen in the presence of a palladium, ruthenium, rhodium, osmium, iridium, platinum, platinum black, palladium black, iron, or cobalt-nickel hydrogenation catalyst in a reaction vessel, thereby to produce purified terephthalic acid containing 4-carboxybenzaldehyde in an amount of fixed range in a stationary manner at a temperature of 255°–300° C. and under a pressure of 10–110 Kg/cm$^2$ with a partial pressure of hydrogen being 0.5–20 Kg/cm$^2$, the improvement comprising exchanging the hydrogenation catalyst in the reaction vessel in part for a new one when the catalyst is deactivated, and thereafter treating the crude terephthalic acid under a partial pressure of hydrogen smaller than that in the stationary state.

5. The improvement as claimed in claim 4 wherein 20–70% of the deactivated catalyst is exchanged for a new one.

6. The improvement as claimed in claim 4 wherein the hydrogenation catalyst is granulated palladium supported on activated carbon.

* * * * *